United States Patent [19]

Zimmon

[11] Patent Number: 5,308,326
[45] Date of Patent: May 3, 1994

[54] BALLOON TAMPONADE DEVICES AND METHODS FOR THEIR PLACEMENT

[76] Inventor: David S. Zimmon, 7 Farm View Rd., Port Washington, N.Y. 11050

[21] Appl. No.: 781,224
[22] PCT Filed: Jun. 28, 1990
[86] PCT No.: PCT/US90/03684
  § 371 Date: Dec. 30, 1991
  § 102(e) Date: Dec. 30, 1991
[87] PCT Pub. No.: WO91/00752
  PCT Pub. Date: Jan. 24, 1991

Related U.S. Application Data

[63] Continuation-in-part of Ser. No. 372,875, Jun. 28, 1989, abandoned.

[51] Int. Cl.⁵ .................................. A61M 29/00
[52] U.S. Cl. ............................... 604/96; 604/101; 606/192
[58] Field of Search .................. 604/96–101, 604/104; 606/111, 112, 191, 192

[56] References Cited

U.S. PATENT DOCUMENTS

| | | | |
|---|---|---|---|
| 3,046,988 | 7/1962 | Moreau et al. | 606/196 |
| 3,411,506 | 11/1968 | Velasco | 606/192 |
| 4,230,108 | 10/1980 | Young | 604/101 X |
| 4,464,175 | 8/1984 | Altman et al. | 604/99 |
| 4,485,805 | 12/1984 | Foster, Jr. | 604/96 X |
| 4,495,948 | 6/1985 | Shapiro | 128/207.15 |
| 4,512,338 | 4/1985 | Balko et al. | 606/191 |
| 4,522,205 | 6/1985 | Taylor et al. | 128/303.17 |
| 4,752,286 | 6/1988 | Okada | 604/96 |
| 4,795,430 | 1/1989 | Quinn et al. | 604/97 |
| 5,067,497 | 11/1991 | Greear et al. | 604/96 X |
| 5,188,596 | 2/1993 | Condon et al. | 604/101 |

Primary Examiner—Robert A. Hafer
Assistant Examiner—Brian E. Hanlon
Attorney, Agent, or Firm—Woodard, Emhardt, Naughton, Moriarty & McNett

[57] ABSTRACT

Balloon tamponade devices for treating bleeding sites within the upper digestive tract (e.g. esophageal or upper gastric bleeding sites, or duodenal, pyloric or distal gastric bleeding sites) comprise a tube having proximal and distal open ends and at least one inflatable balloon mounted over the tube. Preferably, two balloons are mounted over the tube, and inflation lumens are provided for each. In a device for treating esophageal or upper gastric bleeding sites, the balloons are an esophageal balloon and a gastric balloon. In a device for treating duodenal, pyloric or distal gastric bleeding sites, the balloons are a duodenal balloon and a gastric balloon. A bridle is attached to the tube, and is adapted to extend up the esophagus to allow the device to be secured in place having the proximal open end of the tube positioned within the digestive tract to allow for normal feeding and swallowing functions. A method for placing a balloon tamponade device as generally described above is also described. The device is back-loaded onto an endoscope by passing the endoscope through the open ends of the tube. The endoscope is then passed through the mouth and down the esophagus and used to examine the esophagus and/or other portions of the digestive tract to determine whether or not treatment is required. If treatment is required, the device is advanced along the endoscope and down the esophagus, and the balloon(s) of the device is (are) positioned and inflated to treat the bleeding sites. The endoscope is used to check positioning and then withdrawn. Thereafter, the bridal can be positioned through the nose and connected to a traction device.

24 Claims, 4 Drawing Sheets

BALLOON TAMPONADE DEVICES AND METHODS FOR THEIR PLACEMENT

RELATED APPLICATIONS

This is a continuation-in-part of U.S. patent application Ser. No. 372,875 filed Jun. 28, 1989 abandoned Aug. 7, 1990.

BACKGROUND OF THE INVENTION

The present invention relates generally to the treatment of bleeding sites within the digestive tract, and more particularly to esophago-gastric and gastroduodenal balloon tamponade devices, and methods for their placement and maintenance in position. This invention also relates to methods for delivering therapeutic substances using these devices.

It is often necessary to medically treat bleeding sites within the esophagus. One method which has been used to treat such bleeding sites is to exert pressure on them using a balloon tamponade device. Such a device has included a balloon mounted over a tube which can be advanced down the esophagus. Then, the balloon is inflated and used to provide pressure to the site. Serious complications can occur when a device is incorrectly placed and inflated, sometimes producing esophageal rupture. More commonly, the devices are inappropriately placed and are thus ineffective to properly treat the bleeding sites. It is therefore desirable to have a device which can be used in connection with an endoscope so that the placement procedure can immediately follow diagnostic endoscopy and be directly monitored. Additional complications can arise because tamponade devices of the prior art block the esophagus so that normal feeding and swallowing by the patient is impossible and gastric lavage is difficult. This may be especially true where, as in the prior art known to applicant, the tube over which the balloon is mounted extends completely up and out of the patient's esophagus when the device is in place. This arrangement leaves no convenient passage through the mouth to the stomach.

Among the prior art devices, U.S. Pat. No. 4,464,175 to Altman et al. discloses a balloon-tube assembly comprising a multipurpose tamponade and thrombosclerotherapy tube. The tube has an open proximal end and windows spaced approximately 1.5 centimeters from a closed distal end. A modified metal cap diaphragm fits into the tubes open proximal end, and a latex balloon mounted over the tube is connected to a manometer by means of a polyvinyl catheter. The Altman et al. patent describes that the device therein permits effective gastric lavage at the same time that controlled esophageal tamponade is taking place. The device of Altman et al., however, is generally bulky and thus may be more difficult to place and as well uncomfortable to the patient. Additionally, a device such as that disclosed in Altman prevents normal feeding and swallowing functions because of its closed distal end and because its proximal end extends up the esophagus and out of the patient's mouth. As noted, this arrangement provides no convenient passage through which materials may pass to the stomach. Moreover, as disclosed, the Altman device is intended for brief use during gastric lavage and endoscopic sclerotherapy with accompanying tamponade. The Altman device is positioned through the mouth, has no method for prolonged maintenance of its esophageal position, and is intended to be withdrawn immediately after sclerotherapy.

U.S. Pat. No. 4,752,286 to Okada discloses a small diameter (O.D. approx. 2.7 to 4.0 mm) double lumen balloon tube which may be directed through the esophagus prior to the treatment of a varix therein. According to the Okada patent, the varix is thereafter punctured and the balloon tube is partially withdrawn to position the balloon adjacent the punctured varix. Then, an inflation lumen is used to inflate the balloon to provide pressure to check the bleeding. Okada discloses that the other lumen of the device therein may be equipped with suction holes on either side of the varix-compressing balloon. As described in Okada, suction holes proximal of the balloon can be used to remove saliva which collects proximal to the balloon during blood checking, and suction holes distal to the varix-compressing balloon can be used to intake and remove air, blood, and other body fluids. The Okada patent discloses that a stomach balloon can also be provided on the device therein. While providing some advantages, having suction holes as described in Okada does not provide for normal feeding and swallowing functions. Additionally, the Okada device is closed on the distal end and thus its use in connection with an endoscope is limited.

Other devices in the field known to applicant, including, for instance, the Linton and Sengstaken-Blakemore devices, all suffer from one or more of the above and other disadvantages.

In addition to the above discussion relating to treatment of esophageal bleeding sites, it is also sometimes necessary to treat bleeding sites at other points within the digestive tract, for instance within the distal stomach, pylorus and duodenum. One prior treatment of such bleeding sites has involved the use of a balloon mounted over an endoscope which is advanced down the esophagus and through the stomach, whereafter the balloon is positioned and inflated to provide pressure to the bleeding site. This treatment, however, can be used only for a brief period because it obstructs the passage of materials from the stomach into the intestine, and accordingly interrupts the normal feeding by the patient. Additionally, this treatment presents the disadvantage of not allowing the balloon to remain in place after the removal of the endoscope.

Therefore, there exists a continued need for devices for treating digestive tract bleeding sites (e.g. esophageal, upper gastric, distal gastric, pyloric and duodenal bleeding sites) which may be even more effectively used in conjunction with an endoscope, and which permit a comfortable, accurate and convenient placement, and normal swallowing and feeding functions while in place providing therapy to accelerate healing and sealing any perforation or laceration until healing can occur. The treated bleeding sites can be erosions or ulcerations of the mucosa or full thickness injuries such as lacerations or perforations. Applicant's invention addresses these needs.

SUMMARY OF THE INVENTION

One embodiment of the present invention relates to a balloon tamponade device for treating upper digestive tract bleeding sites (e.g. esophageal, upper gastric, distal gastric, pyloric or duodenal bleeding sites). The device includes a tube having proximal and distal open ends, and an inflatable balloon mounted over the tube. An inflation lumen for directing pressurized fluid to inflate the balloon is also provided. A bridle is attached to the tube, and is adapted to extend up the esophagus to allow the device to be secured in place having the proximal open end of the tube positioned within the digestive tract to allow for normal swallowing and feeding functions. In one preferred mode, the balloon tamponade device is an esophago-gastric balloon tamponade device for treating esophageal or upper gastric bleeding sites. In another preferred mode, the balloon tamponade device is a gastroduodenal balloon tamponade device for treating duodenal, pyloric or distal gastric bleeding sites.

Another embodiment of the present invention relates to a novel method for placing a balloon tamponade device as generally described above. The device is backloaded onto an endoscope by passing the endoscope through the open ends of the tube. The endoscope is then passed through the mouth and down the esophagus and used to examine the digestive tract (e.g. esophagus, stomach, pylorus and/or duodenum) to determine whether or not treatment is required. If treatment is required, the device is advanced along the endoscope and down the esophagus, whereafter the balloon of the device is positioned and inflated to compress the bleeding sites.

Still another embodiment of the present invention relates to methods for delivering detachable coatings to digestive tract (e.g. esophageal, upper gastric, distal gastric, pyloric or duodenal) bleeding sites to treat the same.

One object of the present invention is to provide improved devices and methods for treating digestive tract bleeding sites.

Another object of the present invention is to provide an improved device for treating esophageal bleeding sites, which, when in place, permits normal feeding and swallowing by the patient and reduces the risk of aspiration during tamponade.

Another object of the present invention is to provide an improved device for treating esophageal bleeding sites, the placement of which can be accomplished during upper gastrointestinal endoscopy as a single procedure.

Another object of the present invention is to provide an improved device for treating esophageal bleeding sites, the placement of which can be facilitated using a guide introducer.

Another object of the present invention is to provide an improved device for treating esophageal bleeding sites, the placement of which can be directly viewed with an endoscope both during and after its introduction as well as at deflation and removal.

Another object of the present invention is to provide an improved method for placing devices or materials for treating esophageal bleeding sites.

Another object of the present invention is to provide an improved method for treating esophageal bleeding sites.

Another object of the present invention is to provide an improved device for treating lower gastric, pyloric or duodenal bleeding sites, which, when in place, permits normal feeding and swallowing by the patient.

Another object of the present invention is to provide an improved device for treating bleeding sites in the lower stomach, pylorus or duodenum, the placement of which can be accomplished during gastrointestinal endoscopy as a single procedure.

Another object of the present invention is to provide an improved device for treating distal gastric or proximal duodenal bleeding sites, the placement of which can be facilitated using a guide introducer.

Another object of the present invention is to provide an improved device for treating distal gastric or proximal duodenal bleeding sites, the placement of which can be directly viewed with an endoscope both during and after its introduction as well as at deflation and removal.

Another object of the present invention is to provide an improved method for placing devices or therapeutic materials for treating distal gastric, pyloric or duodenal bleeding sites.

Another object of the present invention is to provide an improved method for treating distal gastric or proximal duodenal bleeding sites.

Another object of the invention is to provide devices and methods which help to prevent infection, accelerate healing and seal any perforation or laceration at a bleeding site or at a site without bleeding that could be dangerous.

Related objects and advantages of the present invention will come to light in reviewing the following written specification and accompanying drawings.

DESCRIPTION OF THE PREFERRED EMBODIMENT

Figure 1:
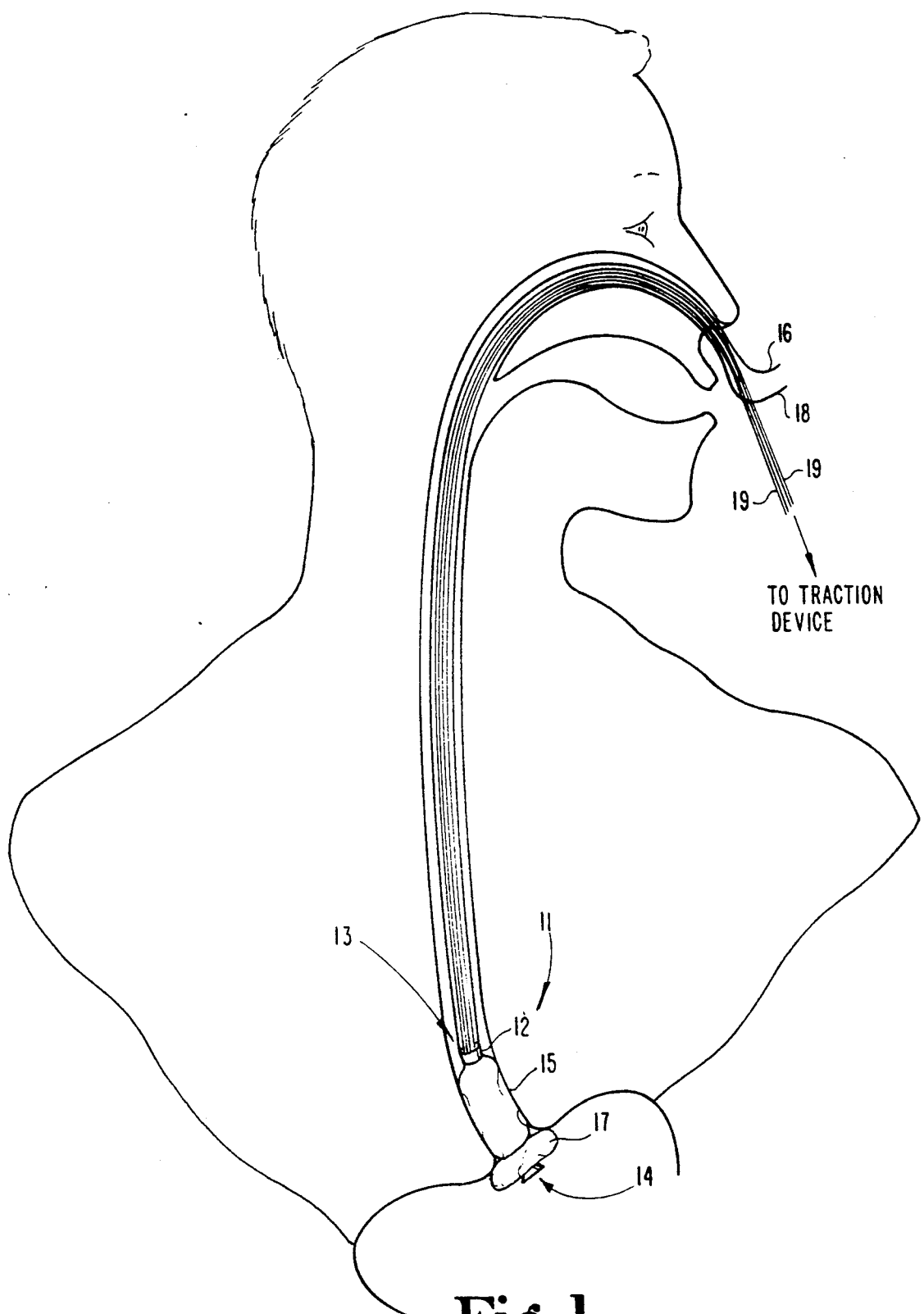
FIG. 1 is a perspective view of a balloon tamponade device according to the present invention in place in a patient.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As stated above, one preferred embodiment of this invention involves a balloon tamponade device for treating digestive tract bleeding sites. The device includes a tube having proximal and distal open ends, and an inflatable balloon mounted over the tube. An inflation lumen for directing pressurized fluid to inflate the balloon is also provided. A bridle is attached to the tube, and is adapted to extend up the esophagus to allow the device to be secured in place having the proximal open end of the tube positioned within the digestive tract to allow for normal swallowing and feeding functions.

In one preferred mode, the balloon tamponade device is an esophago-gastric balloon tamponade device for treating esophageal or upper gastric bleeding sites. Referring now to FIG. 1, shown is a perspective view of such a balloon tamponade device 11 according to the present invention in place in a patient. The device 11 includes a tube 12 having a proximal open end 13, and a distal open end 14. An inflatable esophageal balloon 15 is mounted over the tube, and an inflation lumen 16 is provided for directing pressurized fluid to inflate the esophageal balloon 15.

Four wires 19 are attached to the tube 12 and generally form a bridle. The wires 19 extend up the esophagus to allow the device 11 to be secured in place while having the proximal open end 13 of the tube 12 positioned within the esophagus. A gastric balloon 17, is mounted over the tube 12 and is adapted to seat against the gastric cardia when inflated in the stomach and when thereafter the device 11 is pulled with the wires 19 in a direction up the esophagus. A separate inflation lumen 18 is provided to inflate the gastric balloon 17.

Referring now more particularly to FIG.'s 2-4, the tube 12 of the applicant's preferred device 11 may be made of plastic or another suitable material. The tube 12 is generally of a length so that when the device 11 is in place the tube 12 does not extend upwardly out of the esophagus of the patient. The tube 12 is also sufficiently rigid so that when the esophageal balloon 15 and gastric balloon 17 are inflated, the tube 12 does not collapse, but rather continues to provide a passage through its inner lumen. In applicant's preferred embodiment, the tube 12 is approximately 8 centimeters in length and is translucent or substantially transparent. Additionally, in a preferred embodiment, the tube 12 contains an imbedded wire coil 22 to render the device visible by X-Ray to monitor its position in the patient. The coil 22 may also serve to help prevent the collapse of the tube 12.

Figure 2:
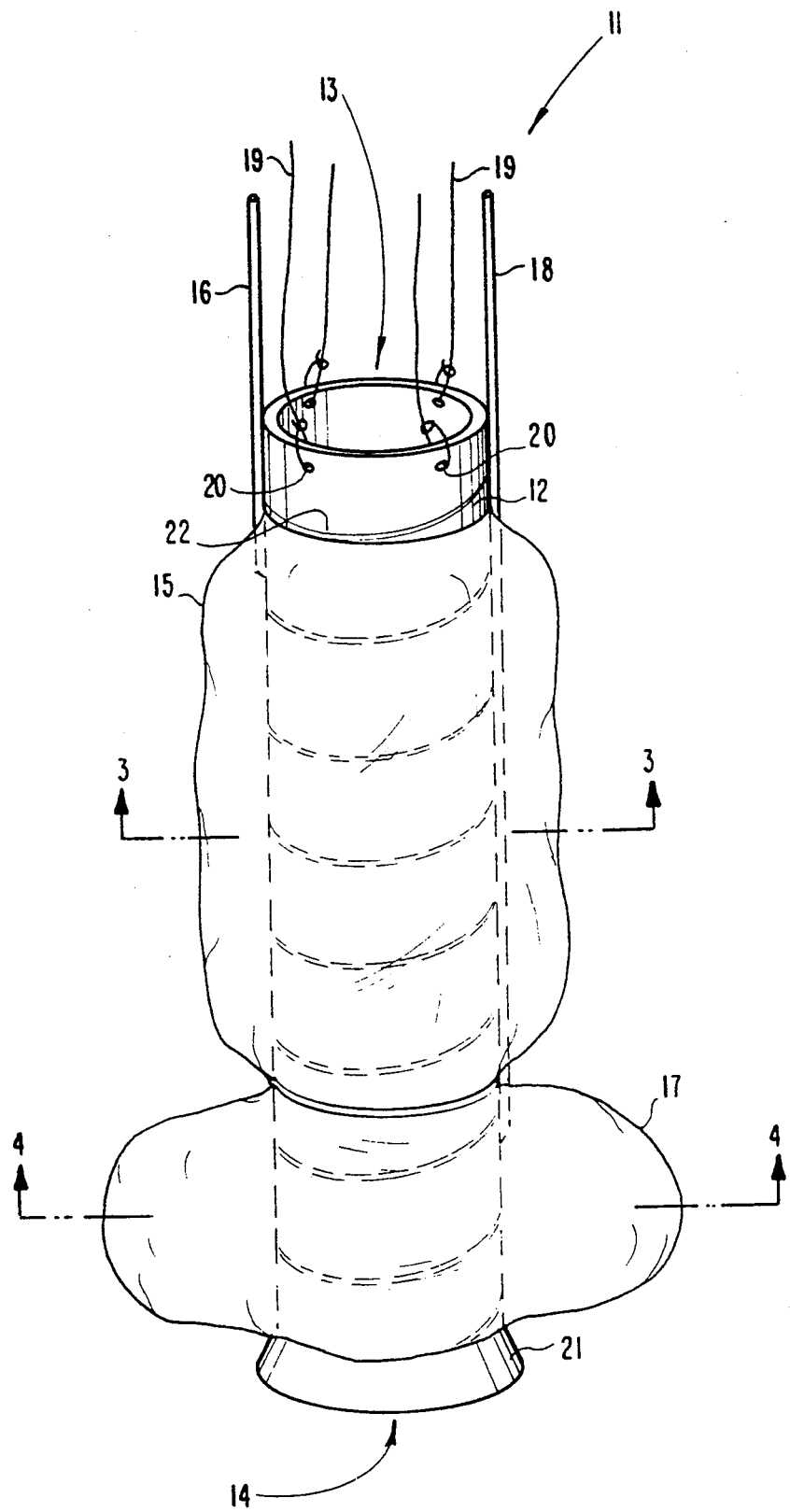
FIG. 2 is an enlarged perspective view of the balloon tamponade device illustrated in FIG. 1. For illustrative purposes, the full lengths of the wires 19 and of the lumens 16 and 18 are not shown.
Figure 3:
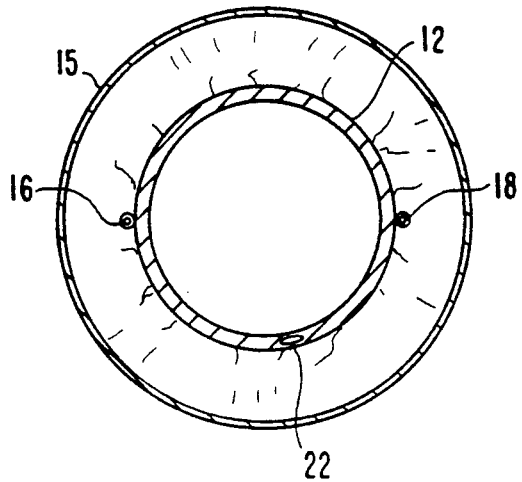
FIG. 3 is a cross-sectional view of the device of FIG. 2 taken along line 3-3 and viewed in the direction of the arrows.
Figure 4:
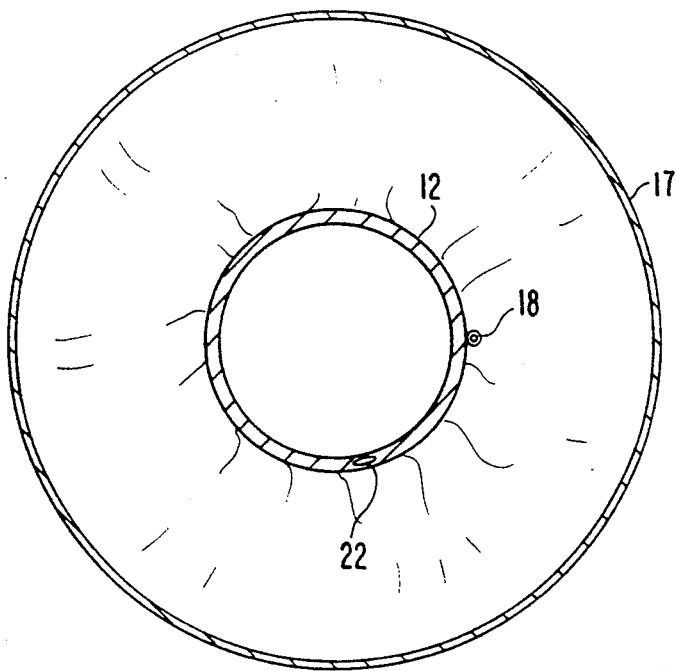
FIG. 4 is a cross-sectional view of the device of FIG. 2 taken along line 4-4 and viewed in the direction of the arrows.

It is also preferred that the tube have an inner diameter of about 1.5 cm and an outer diameter of about 2.0 cm. The 1.5 cm inner diameter is preferred so that even the largest operating upper gastrointestinal endoscopes can be effectively used in connection with the device 11. It is understood, however, that tubes having other dimensions could be used within the scope of the invention herein. Additionally, as illustrated in FIG. 2, the tube 12 may have a flange 21 near its distal open end 14. The flange 21 functions to stabilize the gastric balloon 17.

Turning now to the inflatable esophageal balloon 15 which is mounted over the tube 12, in applicant's preferred device, the esophageal balloon 15 has a length of about 5 centimeters. In the applicant's preferred device 11, this facilitates the effective treatment of the distal most 5 cm of the esophagus (the 5 cm of the esophagus closest to the gastro-esophageal junction), which generally contain the most bleeding sites. Also, in the applicant's preferred device, the esophageal balloon 15 has been of a size such that when inflated, the greatest outer diameter of the device 11 along the inflated esophageal balloon 15 is about 3.0 cm. It is understood, however, that the size of the esophageal balloon 15 can be varied in order to suit a particular patient. As to the means of mounting the balloon over the tube, this may be accomplished by silk ties, bonding or vulcanizing, or any other suitable airtight manner known in the art.

An inflation lumen 16 for directing pressurized fluid to inflate the esophageal balloon 15 is also provided and preferably is bonded to the side of the tube 12. This lumen 16 may be any suitable lumen known in the art for this purpose, and has at least one opening into the esophageal balloon 15 and is of sufficient length to extend up the esophagus and external of the patient when the device is in place.

In applicant's preferred device 11, a gastric balloon 17 is mounted over the tube 12 near its distal open end 14 to provide means for seating within the stomach. The gastric balloon 17 has an inflated diameter which is sufficiently large so that when positioned in the stomach and then inflated, the gastric balloon 17 seats against and compresses the gastric cardia when the device 11 is pulled with the wires 19 in a direction up the esophagus. In applicant's preferred device, the gastric balloon 17 is of a size such that when it is inflated, the greatest outer diameter of the device 11 along the gastric balloon 17 is about 10.0 cm. The gastric balloon 17 can be mounted using silk ties, bonding or vulcanizing, or any other suitable airtight method known in the art. An inflation lumen is also provided to direct pressurized fluid to inflate the gastric balloon 17. This lumen could be the same one which inflates the esophageal balloon 15, but in applicant's preferred devices, a second and separate inflation lumen 18 is provided for the gastric balloon 17, and is also bonded to the side of the tube 12. The inflation lumen 18 passes through the esophageal balloon 15 and into the gastric balloon 17, opening only into the latter. This enables the selective inflation of the esophageal balloon 15 and the gastric balloon 17.

The applicant's preferred device 11 also includes a plurality of wires 19 which are attached to the tube 12 and generally form a bridle. In applicant's preferred device 11, the wires 19 are of sufficient length such that when the device 11 is in place, the wires 19 extend up the esophagus and external of the patient (as more clearly illustrated in FIG. 1). Thus the bridal is adapted and operable to allow the device 11 to be secured in place in the patient while having the proximal open end 13 of the tube 12 positioned within the esophagus. This, in turn, provides a convenient passage through which materials can pass to the stomach and enables normal feeding and swallowing functions. The wires 19 are attached to the tube 12 by securing them through small apertures 20 provided near the proximal open end 13 of the tube 12. It is understood, however, that bonding or any other suitable means known in the art could be used to attach the wires 19 to the tube 12. In applicant's preferred device 11, four wires 19 are provided and attached to the tube 12, but it is understood that three or any other number sufficient to provide stabilization and securing of the device would be adequate. The wires 19 may be constructed of stainless steel or any other suitable material known in the art; however, it is preferred that they be made of or comprise a suitable radiopaque material, such as platinum, to aid in monitoring the placement of the device 11.

As indicated above, another embodiment of the applicant's invention relates to a novel method of placing applicant's devices. In applicant's preferred method, the placement of the device 11 can be accomplished during upper gastrointestinal endoscopy as a single procedure. Prior to passing an endoscope down the esophagus, the device 11 is backloaded on the endoscope. The endoscope is then passed through the patient's mouth and down the esophagus to determine whether and/or where there are esophageal bleeding sites which need treatment. If treatment is necessary, the endoscope is left positioned down the esophagus, and the device 11 is advanced down over the endoscope using a split overtube or the like until the gastric balloon 17 is positioned within the stomach, leaving at least a portion of the wires 19 remaining external of the patient. Thus, the endoscope acts as an internal guide to assist in properly placing the device 11. In most normal adults, when the overtube has been advanced to a distance of 36 cm, the gastric balloon 17 will be positioned in the stomach. The gastric balloon 17 is then inflated and the bridle wires 19 are pulled until the gastric balloon 18 is felt to seat against the gastric cardia. In some situations, for instance in the case of gastric bleeding sites near the gastro-esophageal junction, effective treatment may be provided simply by having the gastric balloon 17 thus in place. If it is determined that additional treatment is necessary or desirable, the esophageal balloon 15 can then be inflated.

A significant advantage of using an endoscope as a guide means is that the endoscope can be used to monitor position of the device 11 both during and after the placement procedure. Such endoscopic monitoring of position and efficacy at initial placement facilitates immediate adjustment or alternate therapy if necessary. In one of applicant's favorite methods, after the device 11 is in place, an endoscopic "U" turn is performed in the stomach to view the placement of the device from below. Thereafter, when, as preferred, the tube 12 is translucent or substantially transparent, the endoscope may be withdrawn into the tube 12 and the placement of the device 11 also viewed from within. Additionally, the endoscope can be used to directly observe mucosa both before and during removal of the device 11 to ascertain if bleeding recurs when the balloons are deflated or when the device 11 is repositioned.

As alternative methods of placement, the device 11 may be placed using a balloon introducer such as model number WCPI-1 Prosthesis Introducer manufactured by Wilson-Cook Medical, Inc., of Winston-Salem, North Carolina, or, during a preceding endoscopy, a wire guide can be passed, and the device 11 can be introduced loaded on a dilator such as a Savary dilator such as model number SGD 14-100 also manufactured by Wilson-Cook Medical, Inc.

Additionally, prior to advancing the device 11 down the esophagus, suitable hemostatic (such as microfibrillar collagen hemostat), coagulant (such as Thrombin, USP), or cytoprotective (such as sucralfate) substances can be applied to the esophageal balloon 14 and/or the gastric balloon 17. Such applications would facilitate effective removal of the device by preventing adherence of the balloons 15 and/or 17 to the bleeding sites.

Still further aspects of the applicant's preferred method of placing its device 11 relate to the securing of the bridle. Once it has been confirmed that the device 11 is properly in place, a flexible guide tube having first and second open ends is provided. The first end of the guide tube is then placed through the nose and out the mouth of the patient, with the second end of the guide tube remaining external of the nose. Thereafter, the bridle wires 19 and inflation lumens 16 and 18, which are extending out of the mouth, are passed into said first end and out said second end of the guide tube. The guide tube is thereafter be withdrawn from the nose, thus leaving the bridle wires 19 and lumens 16 and 18 positioned through the patient's nose.

This stage of the procedure is generally shown in FIG. 1. The gastric balloon 17 and esophageal balloon 15 are inflated, and the wires 19 and inflation lumens 16 and 18 are extending out of the nose. The appropriate connectors can then be placed on the inflation lumens 16 and 18 and the bridle wires 19 can be connected to a traction device as necessary. Having the lumens 16 and 18 and the bridle wires 19 thus positioned through the patient's nose increases patient comfort and reduces trauma to the nose and pharynx as compared to nasal passage of larger previously used devices. Additionally, the wires 19 do not interfere with the use of an endoscope to periodically check the positioning of the device 11.

The device 11 can also be used to deliver and apply detachable coatings to treat bleeding sites, such as expandable mesh, foil or gel. As examples, a suitable expandable mesh is available from Sterile Products of Valley Park, Mo., and known as Xeroform. A suitable foil is available from Deseret Medical & Company and known as Oxycel or from United States Surgical Corporation and known as Helistat. A suitable gel is available from Alcon Laboratories and known as Avitene, or from Parke-Davis and known as Thrombin, USP.

To deliver expandable mesh, the mesh can be mounted over the esophageal balloon 15 by laying it on the deflated balloon while softened with a suitable solvent to conform to the shape of the deflated balloon. The mesh material would then expand to its full size on balloon inflation. Alternatively, the mesh material could be applied to the balloon in a cylinder of strips that overlap so that they could expand when the balloon was inflated. The entire mesh assembly could be protected by a gel coating, sleeve, or peel-away wrapper during passage through the mouth and esophagus into position before inflation. Similarly, to deliver foil, the foil can be mounted over the balloon in a fashion identical to the mesh. The gel can be applied to the balloon and dried in place or applied immediately prior to introduction. If necessary, the gel could be protected by a sleeve or peel-away wrapper during introduction.

Thereafter, the device 11 can be advanced to position the esophageal balloon 15 next to the bleeding sites, and the balloon 15 can be inflated. The mesh, foil, or gel would then contact and adhere to the bleeding sites. The balloon 15 of the device 11 can then be deflated, and the device 11 removed, leaving the detachable coating at the bleeding sites.

When being used to deliver detachable coatings or therapeutic substances, as alternatives to using a balloon in the device 11, other expandable means, for instance, an umbrella-like expandable device activated by hand, spring, screw or hydraulic pressure could also be used as known in the art. Illustrative of this type of device would be the Henning umbrella-type esophageal dilator.

Figure 5:
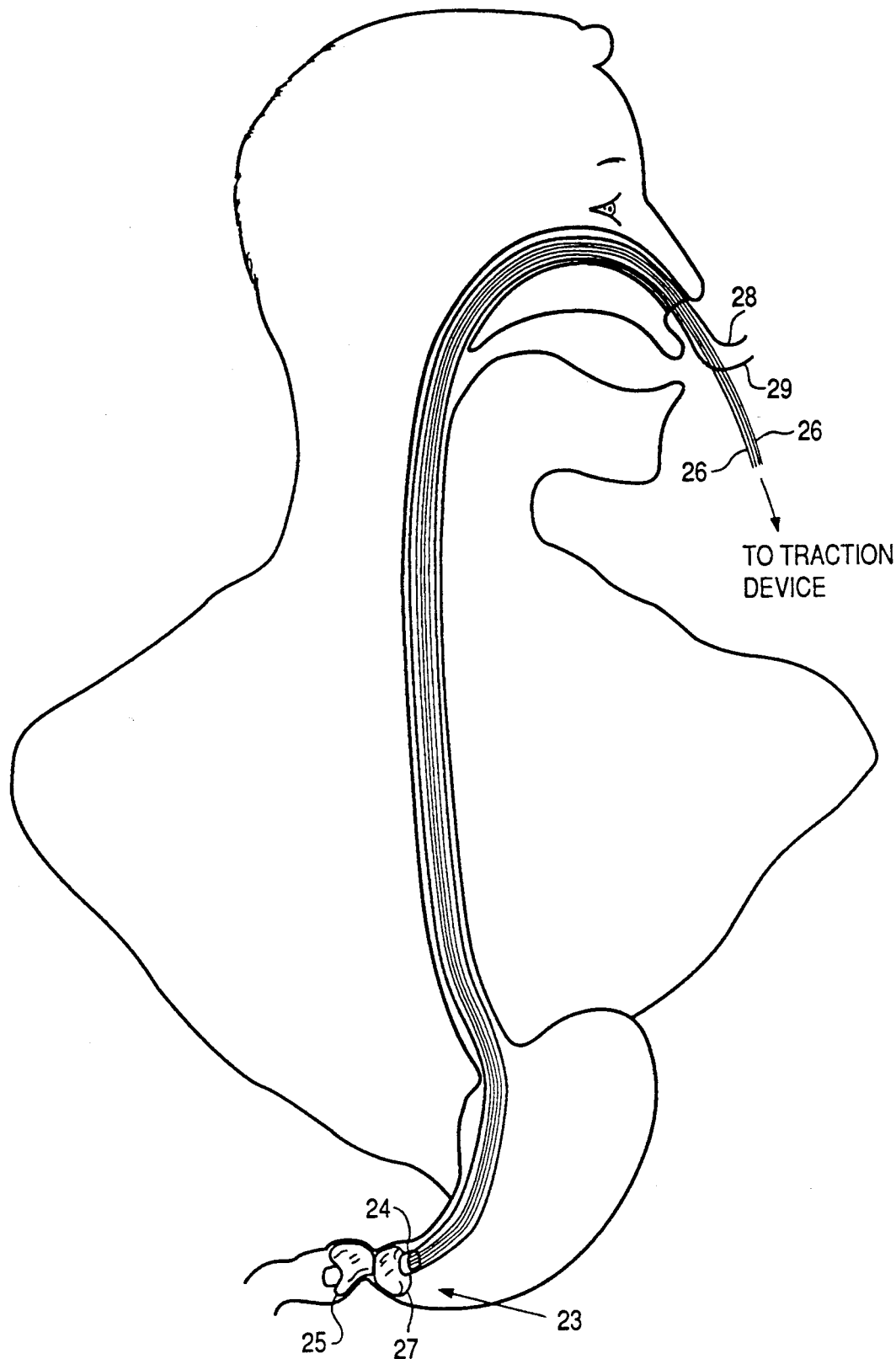
FIG. 5 is a perspective view of a gastroduodenal balloon tamponade device according to the present invention in place in a patient.

As indicated above, in another preferred mode, the applicant's device for treating digestive tract bleeding sites is a gastroduodenal balloon tamponade device for treating duodenal, pyloric or distal gastric bleeding sites. Referring now to FIG. 5, shown is a perspective view of such a gastroduodenal balloon tamponade device 23 in place in a patient. The gastroduodenal balloon tamponade device 23 is similar in construction to the device 11 illustrated in FIG.'s 1-4. However, the preferred dimensions of components of the gastroduodenal device 23 are, of course, altered to suit the dimensions of the areas in which the device 23 is normally used (i.e. the lower stomach and duodenum). Accordingly, the device 23 includes a tube 24 which is generally of a length so that when the device 23 is in place the tube 24 extends across the pylorus. In a preferred embodiment, the tube 24 is about 6 centimeters in length but, unlike the preferred device 11 does not include a significant flange near its distal open end. Such a flange might impede the device's 23 crossing of the pylorus, and thus is not included in the preferred device 23.

The gastroduodenal balloon tamponade device 23 also includes an inflatable duodenal balloon 25 of a size such that when positioned in the duodenum and then inflated, and when the device 23 is then pulled in a direction back toward the stomach by its wires 26, the duodenal balloon 25 seats against and compresses the pylorus and gastric antrum. In the preferred device 23, the duodenal balloon is sized so that when inflated, the greatest outer diameter of the device 23 along the duodenal balloon 25 is about 5 cm. Additionally, the duodenal balloon in the preferred device 23 is about 3 cm in length. These dimensions can, of course, be varied to suit a particular patient.

The gastroduodenal balloon tamponade device 23 also includes an inflatable gastric balloon 27. In applicant's preferred device 23, the gastric balloon 27 has dimensions such that when the balloon 27 is positioned and inflated in the lower stomach, the balloon 27 compresses distal gastric bleeding sites. The preferred gastric balloon 27 has a length of about 3 cm, and when inflated, the greatest outer diameter of the device 23 along the gastric balloon 27 is about 6 cm. As with the duodenal balloon 25, other gastric balloon 27 sizes can be used to suit particular patients.

The gastroduodenal balloon tamponade device 23 also includes a plurality of wires 26 forming a bridal as well as inflation lumens 28 and 29 for selectively inflating the duodenal balloon 25 and the gastric balloon 27. In the preferred device 23, the wires 26 and the lumens 28 and 29 are sufficiently long to extend through the patient's stomach, up the esophagus and out of the mouth while the device 23 is in place. The bridal is thus adapted to allow the device 23 to be secured in place in the patient while having the proximal open end of the tube 24 position within the stomach. This allows convenient passage of materials from the stomach to the intestine and thus enables normal feeding and swallowing functions.

Additional aspects of the construction of the preferred gastroduodenal balloon tamponade device 23 are analogous to those for the preferred esophago-gastric balloon tamponade device 11 described above.

Another embodiment of the invention as indicated above relates to a method of placing the preferred gastroduodenal balloon tamponade device 23. Generally, this method is analogous to the method described above for placing the preferred esophago-gastric balloon tamponade device 11 with appropriate modification being made, of course, to account for the placement of the device in the duodenum and lower stomach as opposed to the distal esophagus and upper stomach.

Accordingly, the device 23 can be placed during gastrointestinal endoscopy as a single procedure. The device 23 is backloaded onto an endoscope prior to passing the endoscope down the esophagus and through the stomach to determine whether and/or where there are distal gastric, pyloric or duodenal bleeding sites needing treatment. In the event that treatment is needed, the endoscope is positioned in the duodenum and the device 23 is advanced down over the endoscope with a split overtube or using another suitable means for advancing. The advancing is continued until the duodenal balloon 25 is positioned in the duodenum, leaving a portion of the wires 26 and the lumens 28 and 29 of the preferred device 23 external of the patient. Approximately a 70 cm advancement of the device 23 will be sufficient to position the duodenal balloon 25 in the duodenum in most normal adults. This figure will of course vary among patients, and appropriate endoscopic or other known monitoring techniques can be used to assist in the placement of the device 23. Once positioned in the duodenum, the duodenal balloon 25 is then inflated and the bridal wires 26 pulled until the duodenal balloon 25 is felt to seat against the pylorus. Where a patient has bleeding sites in the proximal duodenum, effective treatment can be provided by having just the duodenal balloon 25 thus in place compressing the proximal duodenum. If it is determined that additional treatment in the lower stomach is necessary, the gastric balloon 27 can then be inflated.

In an analogous fashion to the placement of the esophago-gastric tamponade device 11 above, the use of an endoscope as a guide means for placement of the device 23 provides the capability of monitoring the position of the device before and during final placement, as well as upon deflation of the balloons and removal. Additionally, the gastroduodenal tamponade device 23 can also be placed using guide means other than an endoscope, such as a balloon introducer. Also, the bridal wires 26 and lumens 28 and 29 of the gastroduodenal tamponade device 23 can be secured as described for the corresponding components of the device 11 above, and the device 23 can be used to deliver and apply to the lower stomach or duodenum suitable hemostatic or other therapeutic substances such as gels, meshes or foils as described above.

Additional aspects of the use and placement of the duodenal balloon tamponade device 23 are analogous to those described above for the esophago-gastric tamponade device 11.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A balloon tamponade device for treating bleeding sites within the digestive tract, said device comprising:
   a tube having proximal and distal open ends;
   a bridle attached to aid tube, said bridle adapted to extend up the esophagus to a traction means, said bridle adapted to secure and position said proximal open end of said tube within the digestive tract to permit normal feeding and swallowing function;
   a first inflatable balloon mounted over said tube; and
   a first inflation lumen opening into said first inflatable balloon, for directing pressurized fluid to inflate said first balloon.

2. The device of claim 1 wherein said first balloon is an inflatable gastric balloon.

3. The device of claim 1 which is for treating esophageal or upper gastric bleeding sites, and wherein said first balloon is an inflatable esophageal balloon.

4. The device of claim 2 which is for treating esophageal or upper gastric bleeding sites, and which additionally comprises:

a second inflatable balloon mounted over said tube between said gastric balloon and said proximal open end, said second inflatable balloon being an inflatable esophageal balloon; and a second inflation lumen opening into said second inflatable balloon, for directing pressurized fluid to inflate said esophageal balloon;

said bridle being adapted to extend up the esophagus to allow said device to be secured in place while having said proximal open end of said tube positioned within said esophagus.

5. The device of claim 4 wherein said bridle comprises a plurality of wires attached to said tube near said proximal open end.

6. The device of claim 5 wherein said tube has an inner diameter of about 1.5 cm.

7. The device of claim 6 wherein said tube is approximately 8 cm in length.

8. The device of claim 7 wherein said gastric balloon is mounted near said distal open end of said tube.

9. The device of claim 8 wherein said esophageal balloon is approximately 5 cm in length and is mounted immediately adjacent to said gastric balloon.

10. The device of claim 9 wherein said tube is substantially transparent.

11. The device of claim 10 additionally comprising a generally helically-wound spring embedded in said tube.

12. The device of claim 11 wherein said spring comprises a suitable radiopaque material.

13. The device of claim 12 wherein said wires comprise a suitable radiopaque material.

14. The device of claim 1 which is for treating duodenal or pyloric bleeding sites, and wherein said first balloon is an inflatable duodenal balloon.

15. The device of claim 2 which is for treating duodenal, pyloric or distal gastric bleeding sites, and which additionally comprises:

a second inflatable balloon mounted over said tube between said gastric balloon and said distal open end, said second inflatable balloon being an inflatable duodenal balloon; and a second inflation lumen opening into said second inflatable balloon, for directing pressurized fluid to inflate said duodenal balloon;

said bridle being adapted to extend up the esophagus to allow said device to be secured in place while having said proximal open end of said tube positioned within the stomach.

16. The device of claim 15 wherein said bridle comprises a plurality of wires attached to said tube near said proximal open end.

17. The device of claim 16 wherein said tube has an inner diameter of about 1.5 cm.

18. The device of claim 17 wherein said tube is approximately 6 cm in length.

19. The device of claim 18 wherein said gastric balloon is mounted near said proximal open end of said tube.

20. The device of claim 19 wherein said duodenal balloon is approximately 3 cm in length and is mounted immediately adjacent to said gastric balloon.

21. The device of claim 20 wherein said tube is substantially transparent.

22. The device of claim 21 additionally comprising a generally helically-wound spring embedded in said tube.

23. The device of claim 22 wherein said spring comprises a suitable radiopaque material.

24. The device of claim 23 wherein said wires comprise a suitable radiopaque material.

* * * * *